US008238636B2

(12) United States Patent
Roell

(10) Patent No.: US 8,238,636 B2
(45) **Date of Patent: *Aug. 7, 2012**

(54) DEVICE, METHOD AND COMPUTER-READABLE STORAGE MEDIUM FOR GENERATING AN EXPOSURE PLAN TO IMPLEMENT RADIATION THERAPY

(75) Inventor: Stefan Roell, Seigendorf (DE)

(73) Assignee: Siemens Aktiengesellschaft, Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 13/113,225

(22) Filed: May 23, 2011

(65) Prior Publication Data

US 2011/0222661 A1 Sep. 15, 2011

Related U.S. Application Data

(63) Continuation of application No. 11/745,518, filed on May 8, 2007, now Pat. No. 7,995,826.

(30) Foreign Application Priority Data

May 10, 2006 (DE) ........................ 10 2006 021 771

(51) Int. Cl.
*G06K 9/00* (2006.01)

(52) U.S. Cl. ........................................ 382/131

(58) Field of Classification Search ........................ None
See application file for complete search history.

(56) References Cited

U.S. PATENT DOCUMENTS

| | | | |
|---|---|---|---|
| 6,038,283 | A | 3/2000 | Carol et al. |
| 6,173,068 | B1 | 1/2001 | Prokoski |
| 6,393,096 | B1 | 5/2002 | Carol et al. |
| 7,152,060 | B2 | 12/2006 | Borthwick et al. |
| 7,574,251 | B2 | 8/2009 | Lu et al. |
| 7,689,021 | B2 | 3/2010 | Shekhar et al. |
| 7,734,010 | B2 | 6/2010 | Otto et al. |
| 2003/0219098 | A1 | 11/2003 | McNutt et al. |
| 2003/0228040 | A1 | 12/2003 | Oosawa |
| 2005/0041843 | A1 | 2/2005 | Sawyer |
| 2005/0276377 | A1 | 12/2005 | Carol |
| 2006/0074293 | A1 | 4/2006 | Vismeier et al. |
| 2006/0093209 | A1 | 5/2006 | Guetter et al. |
| 2006/0171586 | A1 | 8/2006 | Georgescu et al. |
| 2006/0256915 | A1 | 11/2006 | Otto et al. |
| 2007/0043286 | A1 | 2/2007 | Lu et al. |
| 2007/0081712 | A1 | 4/2007 | Huang et al. |
| 2007/0263769 | A1 | 11/2007 | Roell |
| 2008/0039711 | A1 | 2/2008 | Feilkas et al. |

*Primary Examiner* — Bhavesh Mehta
*Assistant Examiner* — Tahmina Ansari
(74) *Attorney, Agent, or Firm* — Schiff Hardin LLP

(57) ABSTRACT

In a device, method and computer program product for generation of an exposure plan for irradiating a patient, at least one reference data set independent of the patient is provided, from which an attenuation of high-energy radiation upon passage through a reference body can be determined. A patient magnetic resonance image of the patient is adapted using the reference data set and an exposure plan is generated based on the patient magnetic resonance image and the patient-specific attenuation of high-energy radiation upon passage through the patient. The patient-specific attenuation of high-energy radiation upon passage through the patient is determined using the adaptation of the patient magnetic resonance image with the reference data set.

27 Claims, 6 Drawing Sheets

DEVICE, METHOD AND COMPUTER-READABLE STORAGE MEDIUM FOR GENERATING AN EXPOSURE PLAN TO IMPLEMENT RADIATION THERAPY

RELATED APPLICATION

This application is a continuation of U.S. application Ser. No. 11/745,518, filed May 8, 2007 now U.S. Pat. No. 7,995, 826.

BACKGROUND OF THE INVENTION

1. Field of the Invention

The present invention concerns device for generation of an exposure plan, a method for generation of an exposure plan as well as a computer program product.

2. Description of the Prior Art

One possible therapy option for many tumor types (for example for malignant tumors of the prostate, colon, breast, thyroid or central nervous system) is radiation therapy. Tumor tissue is irradiated with ionizing high-energy rays (predominantly high-energy gamma radiation or x-ray radiation, but also electrons, neutrons, protons). For all cited radiation types, the effect of the irradiation is physically based for the most part on the energy transfer in scatter processes that leads to a destruction of tumor tissue. The fact is utilized that tumor tissue is for the most part more radiation-sensitive than the surrounding normal tissue. The therapeutic effect requires high doses, typically of 20 to 100 gray dependent on the tumor type.

In order to keep the side effects low, the exposure is often divided into a number of daily individual doses (fractioning) and is administered over multiple weeks (protraction). Moreover, the exposure is spatially and energetically set such that the radiation predominantly strikes only the malignant, pathological region.

For this purpose, an exposure plan is typically generated using an image of the patient that was generated with a three-dimensional imaging method. Computed tomography images (CT images) are typically used for this. The target volume of the exposure can be established using the CT images and a surrounding tissue to be protected (for example neuronal tissue) can be identified.

Moreover, the intensity values of the image voxels of a CT image (measured in units known as "Hounsfield units") reproduce in good approximation the electron density at the corresponding location in the body of the patient, since the intensity values of the image voxels are based on an absorption of the x-ray radiation at the associated locations. Since, in a therapeutic exposure, the intensity of the interaction of the radiation correlates with the electron density in the body, the attenuation of the radiation upon passage through the body can be calculated relatively simply from a CT image. Due to this property, CT images conventionally have been the preferable type of image for use in the generation of an exposure plan.

Recently, however, increasingly more precise exposure methods (modalities) have been developed, such that the delivery of a majority of the energy of the radiation can be limited to a focus a few millimeters in size and can even be modulated within the focus in the framework of therapy is known as intensity-modulated radiation therapy. The soft tissue contrast of a CT image increasingly is not able to match this possible precision of a therapeutic exposure. A need therefore exists to use, in the exposure plan, other imaging methods that exhibit a better soft tissue contrast.

One possible imaging method that satisfies the requirement of a better soft tissue contrast is magnetic resonance imaging (MR imaging). In such imaging, the contrast depends on the distribution of the spin densities, the interaction of the spins among one another and/or with their environment. A soft tissue contrast can be achieved that lies well above the contrast achievable with a computed tomography system. In the generation of an exposure plan, however, magnetic resonance images exhibit the significant disadvantage that the intensity values of the individual image voxels do not correlate with the electron density at the associated locations, such that the attenuation of the radiation on the path through the body cannot be sufficiently precisely determined from a magnetic resonance image.

One possibility to solve this problem is to acquire both a CT image and an MR image of a patient for an exposure plan. These two images can be registered with one another so that the image information of both images can be set in relation to one another. Due to the good soft tissue contrast, the target volume to be irradiated can be precisely localized from the MR image, and the attenuation of the radiation on the path through the body toward the target volume can be precisely determined from the CT image. The necessity to operate with two different imaging modalities in parallel, however, is disadvantageous. In addition to an increased radiation exposure for the patient, the parallel employment of the two imaging modalities means a substantially increased time and cost expenditure in the generation of the exposure plan. An adaptation of the exposure plan is often necessary, primarily when a fractioned exposure is implemented. In this case CT and MR images of the patient must be repeatedly acquired, and the disadvantages of this method become even more manifest.

Furthermore, methods are known in which anatomical structures in MR images are associated with attenuation coefficients. These methods are based on the assumption that deviations of attenuation coefficients for the specific structures (for example bones) from patient-to-patient are negligible. It is additionally relatively complicated to localize the various tissue types in an MR image—for example via interactive and/or partially automated segmentation methods—and to respectively associate the matching attenuation coefficients with the tissue types. In order to limit the effort associated with this, in practice one is limited to only three tissue types: air, bone and soft tissues. This limitation does not always allow the desired precision in the exposure plan.

SUMMARY OF THE INVENTION

An object of the present invention is to provide a device, a method and a computer program product (computer-readable medium encoded with a date structure) that allow an exposure plan to be implemented that is cost-effective and protective of the patient and that exhibits a high degree of precision with regard the localization of the target volume and the determination of the radiation dose.

The object is achieved in accordance with the invention by a device for generation of an exposure plan for a human or animal patient, having access to at least one reference data set independent of the patient, from which reference data set an attenuation of high-energy radiation upon passage through a reference body can be determined, a unit that adapts (or modifies or calibrates) patient magnetic resonance image of the patient according to the reference data set, and a plan generator that generates an exposure plan dependent on the patient magnetic resonance image and the patient-specific attenuation of high-energy radiation upon passage through the patient, the patient-specific attenuation of high-energy radiation upon passage through the patient being determined using the adaptation of the patient magnetic resonance image with the reference data set.

An exposure plan can be generated using the device when only one magnetic resonance image (a patient MR image) of a patient exists. The patient MR image has the advantage of showing good soft tissue contrast for the exposure plan, such that the localization of the target volume in the patient MR image can be implemented precisely.

The information necessary for the determination of the attenuation of high-energy radiation exists for a reference body and is stored in the reference data set corresponding to the reference body. The image and adaptation unit adapts the patient MR image with the reference data set so that this initial patient-independent information can also be taken into account in the generation of the exposure plan for the patient. By means of the adaptation, the patient MR image is adapted to the reference data set (and therewith also to the reference body) so that the initial patient-independent information about the attenuation of the high-energy radiation can be transferred to the patient MR image through the adaptation, such that the patient-specific attenuation of high-energy radiation upon passage through the patient can be determined. The exposure plan then can be implemented in a next step using the patient MR image and the patient-specific attenuation.

The reference body or the reference data set typically will not represent the entire body, but rather only that part that is relevant for the exposure plan for a specific tumor. This part is adapted to, among other things, the patient MR image. For example, only information as to the attenuation of the radiation in the pelvis minor is necessary for an exposure plan for a primary tumor of the prostate; correspondingly, only an MR image of the pelvis minor is used as the patient MR image. Typically only the information about the attenuation of the radiation in the region of the pelvis minor in the reference body is stored in the reference data set.

In an embodiment the (at least one) reference data set represents a computed tomography image of the reference body.

Since a CT image depicts the electron density in the body of the patient in good approximation, and since the electron density at the same time represents a measure for the attenuation of the high-energy radiation, the attenuation of the radiation by the reference body can be determined relatively simply from a reference data set that represents a CT image. The adaptation of the patient MR image thereby ensues with the computed tomography image of the reference body.

The (at least one) reference data set preferably represents a magnetic resonance image, the magnetic resonance image being an image of the reference body corresponding to the computed tomography image.

Because a magnetic resonance image is also stored in the reference data set, the adaptation of the patient MR image with the reference data set can also be implemented in a simple manner since now an image (the MR image) is stored in the reference data set that exhibits an image contrast more similar to the patient MR image than the CT image.

The image adaptation unit preferably adapts the patient magnetic resonance image with the magnetic resonance image of the reference data set.

The similar image contrast between the patient MR image and the MR image of the reference data set can be utilized in this manner such that the adaptation unit can be fashioned more simply. If, for example, adaptation unit is a program algorithm running in a computer, computer capacity can be saved.

The magnetic resonance image and the computed tomography image of the patient-independent reference data set corresponding to the magnetic resonance image are advantageously registered with one another.

When the MR image and the CT image of the reference data set are already registered with one another, the information about the attenuation of the high-energy radiation that is determined from the CT image can be directly transferred to the MR image of the reference data set. Particularly when the adaptation of the patient MR image ensues with the MR image of the reference data set, the information about the attenuation of radiation can be transferred directly from the CT image to the patient MR image through the MR image of the data set.

In one preferred embodiment, the adaptation unit registrates the patient magnetic resonance image with the reference data set using a rigid and/or elastic registration.

The registration allows a topographical relation of the image voxels of the patient MR image with the reference data set (thus with the CT image or MR image stored there) to be produced, so the information of the attenuation of the high-energy radiation can be transferred directly to the patient MR image.

The reference data set is advantageously part of a databank that contains further similar data sets. The device advantageously administers the databank.

The further similar data sets in the databank can originate from different reference persons and encompass well the spectrum of different anatomical conditions to be expected, thus the reference persons can differ, for example, in terms of size, weight, gender, possibly also in ethnic background and in age.

The device preferably allows for selection of a specific data set as a reference data set from the data sets of the databank, the selected specific data set exhibiting the greatest correlation with the patient magnetic resonance image.

In this manner a specific data set that exhibits the greatest correlation with the patient MR image with regard to specific features can be selected from the databank with regard to the patient MR image. When the data sets of the databank include, for example, CT images and MR images of reference persons, the reference data set is selected by a coordination of the patient size, the patient weight, the gender, the ethnic background of the patient and/or his or her age with the corresponding data of the reference persons. However, it is also possible to evaluate the patient MR image and the MR images of the data sets roughly with regard to coinciding features (size, extent of the shown organs, intensity value distributions) and to thereupon select the data set with the greatest possible correlation as a reference data set.

In another embodiment the reference data set is a reference data set averaged from further multiple sets.

Anatomical peculiarities that always occur to a certain degree thus can be reduced by the averaging. The reference body that is associated with the reference data set is in this case likewise not the body of a single person but rather a virtual body (also called an atlas). Before averaging, the further data sets can be registered with one another so that the averaging is implemented more precisely.

In a preferred embodiment the device includes an evaluation unit that evaluates the adaptation with which the adaptation of the patient magnetic resonance image can ensue with the reference data set.

Whether the adaptation of the patient MR image with the reference data set was sufficiently precise for an exposure plan can be indicated by this evaluation before further implementation of the procedure. For example, the procedure can reach its limits if the patient or the patient MR image exhibits such greatly deviating anatomical peculiarities that an adaptation with a reference data set (and therewith also the exposure plan) can be implemented only insufficiently. Through the evaluation, a user's attention is directed to possible problems so that he or she can intervene and, for example, can arrange further examinations (such as, for example, a CT examination) for the exposure plan.

The above object also is achieved in accordance with the invention by a method for generation of an exposure plan for a human or animal patient that includes the steps of automatically electronically adapting a patient magnetic resonance image of a patient with a reference data set independent of the patient, from which reference data set an attenuation of high-energy radiation upon passage through a reference body can be determined, generating an exposure plan dependent on the patient magnetic resonance image and the patient-specific attenuation of high-energy radiation upon passage through the patient, with the patient-specific attenuation of high-energy radiation upon passage through the patient being determined using the adaptation of the patient magnetic resonance image with the reference data set.

The at least one reference data set preferably represents a computed tomography image that is adapted with the patient magnetic resonance image.

The at least one reference data set furthermore preferably represents a magnetic resonance image, whereby the magnetic resonance image being an image of the reference body corresponding to the computed tomography image.

In this case the adaptation of the patient magnetic resonance image with the reference data set preferably ensues by an adaptation of the patient magnetic resonance image with the magnetic resonance image of the reference data set.

Furthermore, the magnetic resonance image and the computed tomography image of the patient-independent reference data set (which computed tomography image corresponds to the magnetic resonance image) can be registered with one another. This registration can be implemented once and be stored in the reference data set, such that computing capacity is spared since this registration does not have be conducted again every time.

In a preferred embodiment, the adaptation of the patient magnetic resonance image with the reference data set ensues by registering the patient magnetic resonance image with the reference data set using a rigid and/or elastic registration.

An embodiment includes storing the reference data set as part of a databank that contains further similar data sets.

The reference data set is then preferably selected from the databank dependent on the patient magnetic resonance image, such that the patient magnetic resonance image and the reference data set exhibit the greatest possible correlation with regard to specific features.

Another embodiment includes generating the reference data set by averaging further data sets.

A preferred embodiment of the method includes the step, after the adaptation of the patient magnetic resonance image with the reference data set, of evaluating the adaptation, and the method is continued dependent on the evaluation.

In an embodiment of the method a computed tomography patient image is also present for a patient in addition to the patient magnetic resonance image, a first exposure plan is generated with the method as described above, a second exposure plan is generated by joint use of the patient magnetic resonance image and the computed tomography patient image, and a verification ensues by a comparison of the first exposure plan and the second exposure plan.

The method for generation of an exposure plan can be verified in this embodiment of the method, and in fact for patients for whom both a patient MR image and a patient CT image exist. The first exposure plan can be generated (starting from the patient MR image) with a method as described above. The second exposure plan can be generated by joint usage of the patient magnetic resonance image and the computed tomography patient image. Conventionally this manner represented the best method for generation of an exposure plan but it exhibited the disadvantages described above. By a comparison of the first exposure plan and the second exposure plan, a verification (and thus with a quality control) of the method according to the invention can now ensue, for example by assessing the difference between the first exposure plan and the second exposure plan and requiring the difference to be within a tolerance range.

In another embodiment of the method, a data set is determined from the databank as a verification data set (representing a verification MR image and a verification CT image), a first exposure plan is generated based on the verification MR image and the verification MR image is used in place of the patient magnetic resonance image, a second exposure plan is generated based on joint usage of the verification MR image and the verification CT image, and a verification ensues by a comparison of the first exposure plan and the second exposure plan.

In this embodiment of the method the verification ensues using the data sets stored in the databank. The data set determined as a verification data set is thus no longer available as a reference data set in the context of the selection of a specific data set. Since the databank contains multiple data sets, the data set closest to the verification MR image is selected as a reference data set. Here as well the verification ensues by a comparison of the first exposure plan and the second exposure plan in that the difference of the two exposure plans is assessed and must lie within a tolerance range.

The above object also is achieved in accordance with the present invention by a computer program product (a computer-readable medium encoded with a data structure) that, when loaded into a computerized device for generation of an exposure plan, causes the device to implement the above-described method, including any and all embodiments thereof.

DESCRIPTION OF THE PREFERRED EMBODIMENTS

Figure 1:
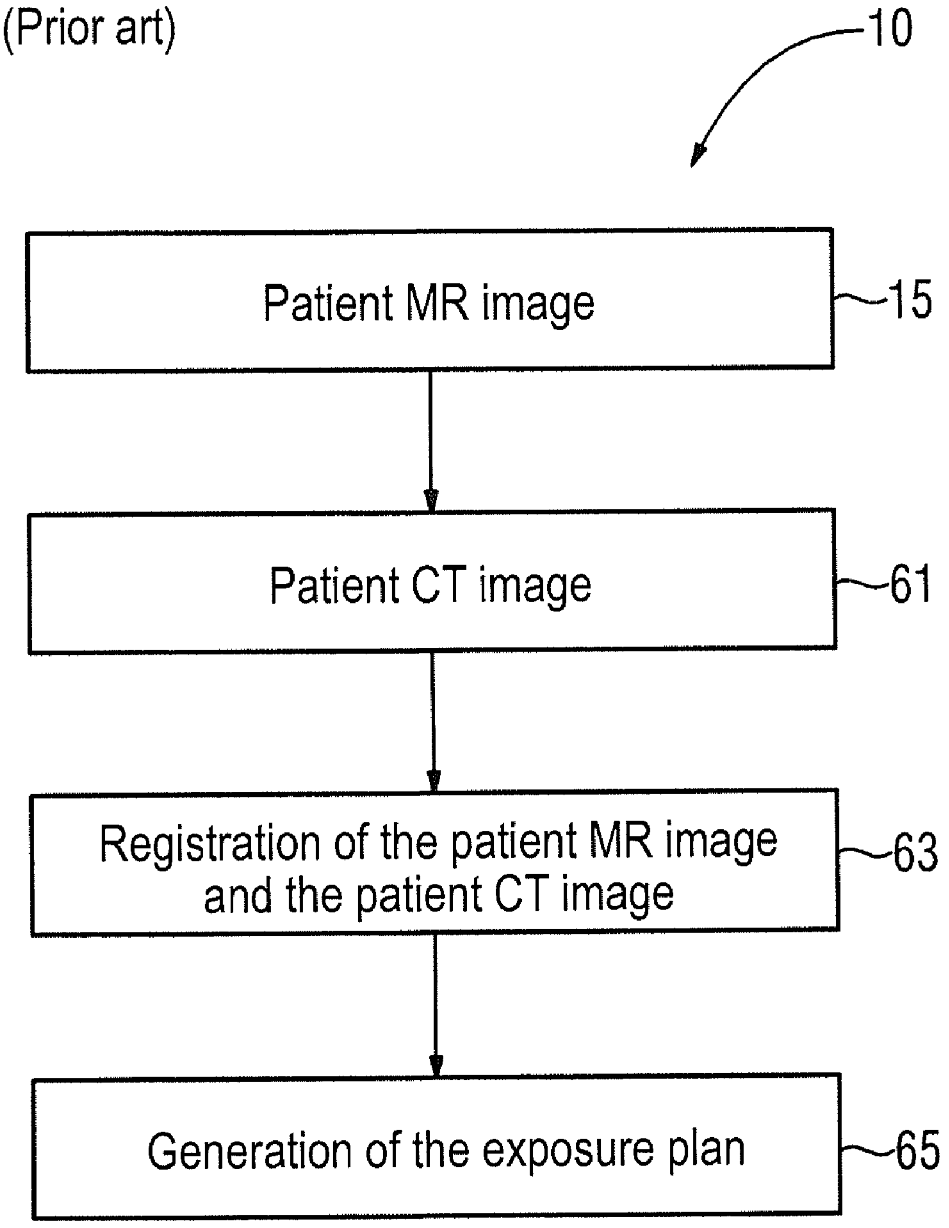
FIG. 1 is a flowchart for a method according to the prior art with which the generation of an exposure plan ensues using a comparison of MR image data and CT image data.
Figure 2:
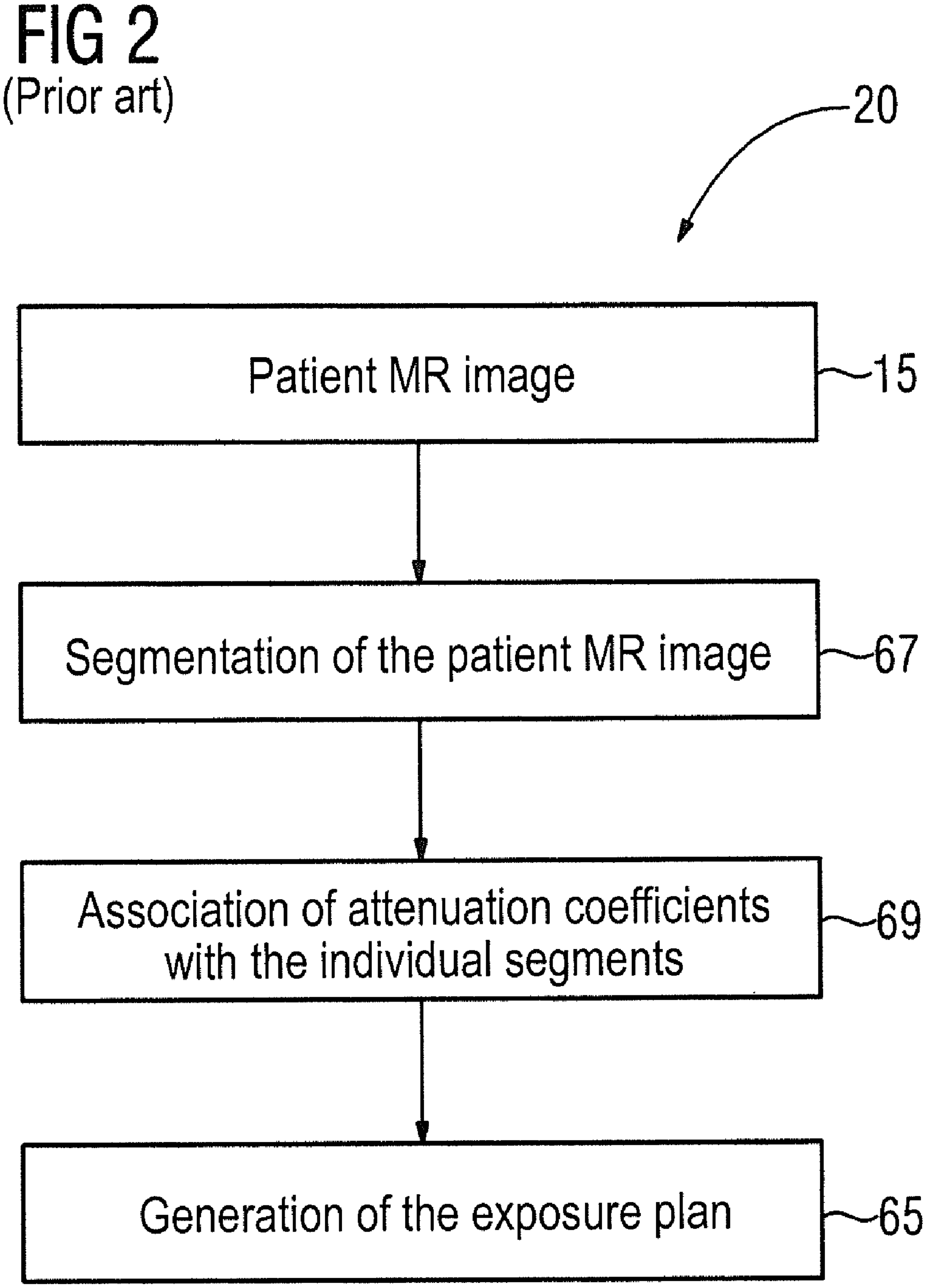
FIG. 2 is a flowchart for a method according to the prior art with which the generation of an exposure plan ensues using a segmentation of an MR image.

FIG. 1 and FIG. 2 show a first method 10 and a second method 20 that are known from the prior art with which the generation of an exposure plan can be implemented using an MR image of the patient (designated in the following as a patient MR image 15).

In addition to the patient MR image 15, in the first method 10 a computed tomography image of the same patient (designated as a patient CT image 61) is produced. In order to compensate for possibly occurring geometric distortions or a slightly deviating position of organs between the patient MR image 15 and the patient CT image 61, a registration 63 of the two images with one another is implemented. An exposure planning 65 for the patient can now be implemented using the images registered with one another, whereby the tumor localization (and therewith the focus of the irradiation) is determined using the patient MR image 15 due to the good soft tissue contrast, and the attenuation of the high-energy radiation on the path through the patient is calculated using the patient CT image 61 and is taken into account in the exposure planning 65.

In the registration, the patient MR image 15 is typically registered on the patient CT image 61, meaning that the patient MR image 15 is transformed such that its image voxels correspond with the image voxels of the patient CT image 61. This achieves a number of advantages. Imaging system-dependent distortions occur less in computed tomography systems than in magnetic resonance apparatuses, in which additional distortions can occur in an MR image due to magnetic field inhomogeneities. Moreover, a radioscopy apparatus with which the exact patient positioning for the treatment can monitored (controlled) is usually already present in a therapy apparatus for radiation therapy. This radioscopy apparatus exhibits a contrast similar to the patient CT image 61, such that an image acquired with this can be directly adapted with the patient CT image 61 without time-consuming registration.

The patient MR image 15 alone forms the basis of the second method 20. After a segmentation 67 of the patient MR image 15, an association 69 of attenuation coefficients into individual segments ensues. The exposure planning 65 can be implemented after this association 69, given which exposure planning 65 the localization of the irradiation focus is implemented using the patient MR image 15 and given which the attenuation of the high-energy radiation on the path through the patient is accounted for using the attenuation coefficients associated with the individual segments.

Both methods exhibit the disadvantages discussed above in the previous description of the prior art.

Figure 3:
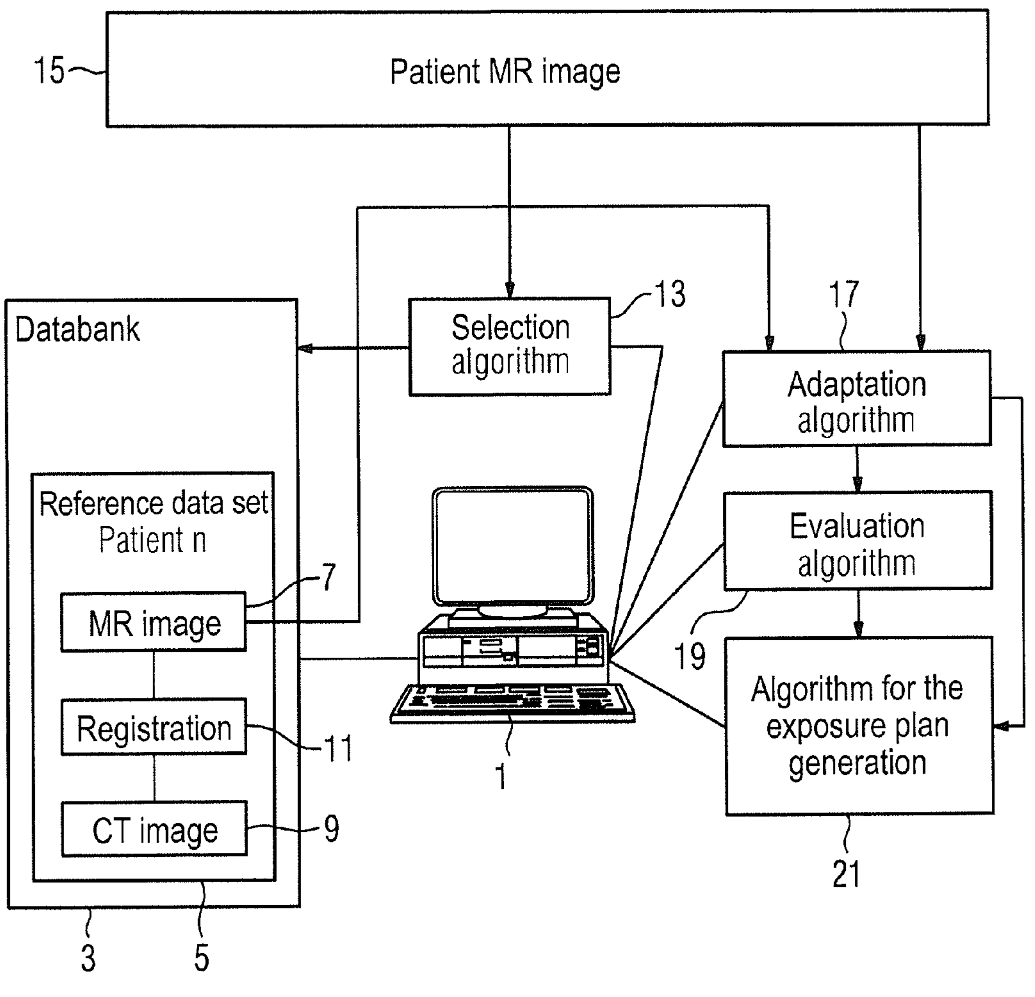
FIG. 3 schematically illustrates an embodiment of the inventive device fashioned as a computer.

FIG. 3 shows an inventive device fashioned as a computer 1, with which inventive device an exposure planning can be implemented.

The embodiment of the inventive device as a computer 1 is advantageous since the computer 1 can be flexibly adapted to the respective needs and requirements of the exposure plan by allowing, for example, specific programmed algorithms to be adapted and altered. The computer 1 additionally allows in a simple manner an interaction with a user, who thus can monitor (and, if applicable, intervene in) important steps in the generation of an exposure plan. The invention, however, is not limited to the embodiment as a computer 1.

The computer 1 is connected with a databank 3. A number of data sets are stored in this databank 3. Shown schematically is an individual reference data set 5 that represents an MR image 7 and a CT image 9 that have been acquired from the same reference person (different from the patient), for example from a patient already treated. Furthermore, the MR image as well as the CT image 9 are registered with one another (co-registered); this first registration 11 is stored as well in the reference data set 5.

The further data sets in the databank 3 are constructed in an analogous manner and can originate from different reference persons and cover optimally well the spectrum of the different anatomical conditions to be expected. The reference persons differ, for example, in their size, weight, gender, possibly also in their ethnic background and their age. Among other things, in the method described later in FIG. 4 an example of how the databank 3 can be administered and possibly expanded is explained in detail.

The registration, for example the first registration 11 that is stored in the reference data set 5, can ensue according to any of a variety of methods with which, given two images that depict the same or a similar subject, an unambiguous topographical relation or correlation is produced between their image elements (pixels or voxels). The determination of the correlation ensues for the most part via prominent features (known as "landmarks") that are determined either interactively by the user or automatically by a system. The landmarks can be one-dimensional structures (such as, for example, special anatomical points) or multi-dimensional structures (such as, for example, surfaces of specific organs that were segmented beforehand in the images). The registration can also ensue on the basis of intensity value distributions represented in the images.

The registration 11 stored in the reference data set 5—as well as the respective registrations in the other data sets—can be a rigid registration and/or an elastic registration. For a rigid registration (also called a rigid body registration), three translation variables and three rotation variables are typically determined, from which the different positioning of the patient during the CT data acquisition and the MR data acquisition is described so it can therewith be compensated. In a next step, an elastic registration of the CT image 9 and/or of the MR image 7 also allows variations in the position and orientation of individual organs to be compensated, up to compressions of individual organs or of the entire body. The selected manner and the precision of the registration are adapted to the medical question and the organ system to be imaged and represent a compromise between the precision of the correlation between the two images and the computation time for determination of the correlation.

As shown in FIG. 3, the matching registration 11 does not have to be stored in one of the data sets in addition to the MR image 7 and the CT image 9. For example, it is also possible to transform one of the two images (for example the CT image 9) with the registration and to store the transformed CT image in the reference data set 5 in place of the original CT image 9. Given sufficient computation power, the registration can also always be calculated "online" when a transformation of the two images is needed.

The computer 1 has a selection algorithm 13 with which a specific data set can be selected from the databank 3 as a reference data set 1 for the adaptation with a patient MR image 15. The reference data set 5 that is selected exhibits the greatest possible correlation with the patient MR image 15 among the data sets stored in the data bank 3. For example, the reference data set 5 can be selected based on the patient size, the patient weight, the gender, the ethnic background of the patient and/or his age with the corresponding data of the reference persons. It is also possible for the patient MR image 15 and the MR images 7 of the data sets to be roughly evaluated with regard to coinciding features (size, expansion of the shown organs, intensity value distributions) and the data set with the greatest possible correlation is thereupon selected as a reference data set 5.

Furthermore, the computer 1 has an adaptation algorithm 17 with which the patient MR image 15 can be adapted with the reference data set 5. In the embodiment presented here, this occurs in that a registration is determined that co-registers the patient MR image 15 with the MR image 7 of the reference data set 5.

Here as well a similar algorithm can be used for the registration, with which similar algorithm the CT image 7 and the MR image 9 of the reference data set 5 can have been registered with one another. A different positioning of the patient and the reference person in the acquisition of the image data can initially be compensated via a rigid registration (thus via translations and/or rotations); the different anatomy of the patient and of the reference person with one another can be correlated with one another via an elastic registration and a conversion can then ensue.

The invention is based on the insight that since the pathological variation (which can turn out to be very different between individuals) often occupies up only a small part of the image volume in an image that is used for the exposure planning, sufficient further structures exist that exhibit a low variation range from person-to-person are depicted as well in the image, so that the registration can be implemented using these structures that are similar between individuals. The method reaches its limits only when the pathological variation occupies too large a portion in the image volume (for example when a tumor illness is far advanced) or when the patient exhibits features that significantly deviate from anatomical norms.

In order to recognize these cases, the computer 1 has an evaluation algorithm 19 with which the found adaptation (in this case the determined registration) is evaluated. The evaluation can ensue in different manners. For example, the strength of the registration that converts the patient MR image 15 and the MR image 7 of the reference data set 5 into one another can be evaluated, for example by determination of the average warp distance that converts corresponding image voxels into one another. When the registration is too complicated, i.e. when transformations that are too large must be applied in order to correlate the two images with one another that can be an indication that the adaptation was insufficiently implemented for the exposure plan. Alternatively or in addition, the remaining difference after an adaptation of the patient MR image 15 with the MR image 7 of the reference data set can be evaluated. When residual differences that are too large are present, this likewise indicates that the adaptation algorithm has reached its limits. In both cases a signal can then be generated that indicates possible problems to the user so that the user can manually intervene.

By the application of the selection algorithm 13 and the adaptation algorithm 17, the patient MR image 15 can be co-registered with the MR image 17 and (through the registration 11 stored in the reference data set 5) also with the CT image 9. The attenuation coefficients for high-energy radiation that can be derived from the CT image 9 can now be associated with the patient MR image 15 in this manner. Since inter-individual differences in the attenuation coefficients for the same tissue type are negligible, the attenuation coefficients for the current patient have also been determined by the adaptation of the patient MR image 15 of the patient with the reference data set 5, with all nuances of the CT image 9 being retained for the determination of the attenuation of the radiation without a computer tomography having to be administered to the patient, such that time and costs are saved and the patient load is reduced.

Furthermore, the computer 1 has an algorithm for the generation of the exposure plan with which the soft tissue contrast of the MR image 15 of the patient is now utilized for localization of the target volume of the exposure, and with which the attenuation coefficients of the CT image 9 of the reference data set 5 (which attenuation coefficients are associated with the MR image 15 of the patient) are determined for the determination of the attenuation of the radiation upon passage through the patient body. Based on this knowledge, the exposure plan can now be generated according to known methods.

Among other things, the establishment of a target volume; the establishment of the reference dose (that dose that is viewed as representative in the target volume); the establishment of the limit dose (that dose that may not be exceeded in a risk range); the calculation of the minimal, maximum or median dose in the target volume and of the dose in risk ranges are among these "known methods". A generated exposure plan can be checked with a simulation and be modified if applicable. Among other things, position and extent of the target volume; the risk organs; the tissue inhomogeneities; as well as body contours or surfaces (that can be determined significantly more precisely with patient MR image 15 than with a CT image due to the good soft tissue contrast) are relevant topographical-anatomical data for an exposure plan.

Figure 4:
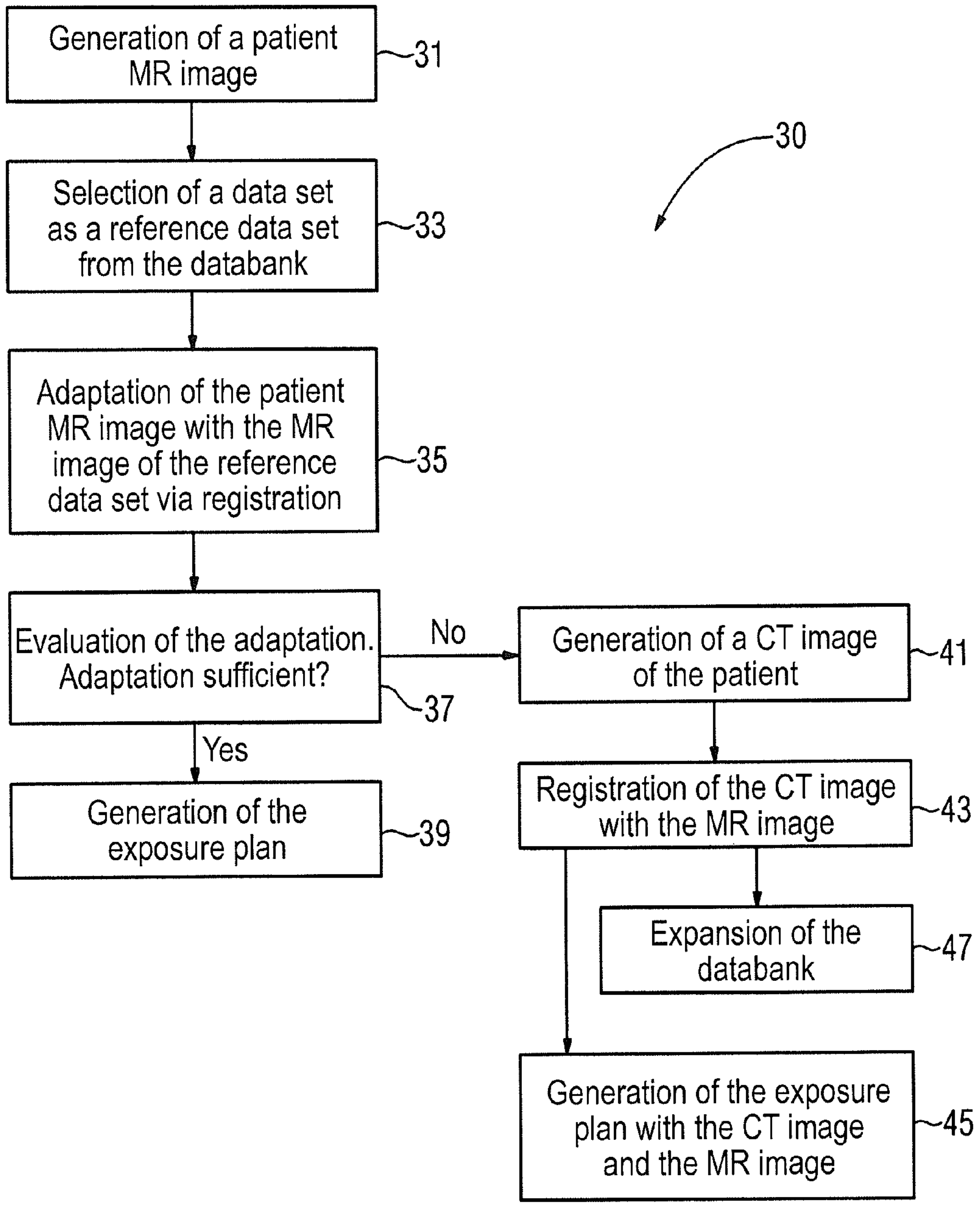
FIG. 4 is a flowchart of the individual method steps of an embodiment for generation of an exposure plan with the inventive device.

FIG. 4 shows a third method 30 that is preferably used in an exposure planning for which the inventive device is employed.

An MR image of the patient (patient MR image 15) is produced in a first method step 31.

The patient MR image 15 is loaded into the memory of the computer 1 which (in a second method step 33) selects a suitable data set from the databank 3 as a reference data set 5 using the selection algorithm 17.

After selection of the reference data set 5, the adaptation of the patient MR image 15 with the reference data set 5 ensues in a third method step 35 using the adaptation algorithm 17. The patient MR image 15 is hereby registered with the MR image 7, as described above.

An evaluation of the adaptation with the evaluation algorithm 19 and (dependent thereon) a decision about the further proceeding ensue in a fourth method step 37. As illustrated above, the evaluation can thereby evaluate the degree or the significance of the registration and/or the remaining differences between the patient MR image 15 and the MR image 7 of the reference data set 5 after a registration has occurred, when the adaptation algorithm uses a registration of the patient MR image 15 to the reference data set 5.

The evaluation can ensue, for example, based on one evaluation measure; when the measure lies within a predefined tolerance range, the adaptation is considered as sufficiently precise. In this case, a patient MR image 15 now exists in which the attenuation of high-energy radiation upon passage through the patient can be additionally calculated since the patient MR image 15 is correlated with the CT image 9 of the reference data set via the MR image 7 of the reference data set 5, and since attenuation coefficients can thus be associated with the individual image voxels of the patient MR image 15.

The algorithm 21 for the generation of an exposure plan can now be implemented in a fifth method step 39.

In the event that the evaluation in the fourth method step 37 leads to the result that the adaptation is not sufficiently precise for an exposure plan, another branch occurs. In a sixth method step 41, a CT image of the patient is produced, since otherwise the attenuation of the radiation can only be insufficiently determined and accounted for given generation of an exposure plan for the patient. In order nevertheless to be able to use the information of the patient MR image 15, in a seventh method step 43 the patient MR image 15 and the CT image of the patient are registered with one another such that the exposure planning can ensue using both co-registered images (eighth method step 45).

Moreover, a further co-registered pair of an MR image and a CT image of the same person now exists, namely the patient MR image 15 and the produced CT image of the patient. Since the computer 1 is connected with the databank 3 and can administer the databank 3, in a ninth method step 47 the databank 3 is expanded with this pair. In this manner the databank 3 is always successively expanded when the exposure planning is effected for a patient whose anatomical properties allow no sufficiently precise adaptation with one of the data sets of the reference persons. In the course of time the databank 3 expands such that the probability to find a matching reference data set 5 for a new patient becomes greater.

In the following a verification method 50 is now illustrated using FIG. 5, which verification method 50 is likewise implemented with the computer 1 shown in FIG. 3 and with which the third method 30 illustrated in FIG. 4 for generation of an exposure plan can be checked with regard to its quality.

A data set with which the verification method 50 is implemented is initially selected from the databank 3; in the following this data set is designated as a verification data set 51. This verification data set 51 represents a CT image and an MR image of a reference person that are registered with one another; in the following these two images are designated as a verification CT image 54 and verification MR image 53. An exposure plan for the verification data set 51 can consequently be generated with a conventional method that is based both on a CT image and on an MR image (designated in the following as CT-MR combination method 55), for example according to first method 10 explained in FIG. 1. With regard to the precision of the exposure plan, the CT-MR combination method 55 represents the standard against which the precision of the third method 30 (FIG. 4) is now measured.

An exposure plan is now generated according to a modified third method 40 for verification MR image 53 of the verification data set 51, whereby the verification MR image 53 is taken in place of the patient MR image 15.

The method steps of the modified third method 40 significantly coincide with the third method 30 shown in FIG. 4, but with the difference that, although the evaluation of the adaptation ensues in the modified third method 40, the method is not terminated if the evaluation were to indicate an insufficiently precise adaptation. A first exposure plan 57 is always obtained at the end of the method in this manner. This exposure plan is now compared with the second exposure plan 59 that was generated with the CT-MR combination method 55.

If the first exposure plan 57 and the second exposure plan 59 coincide within a predefined tolerance range (correspondence 71), the modified third method 40 (and therewith also the third method 30) supplies a sufficiently precise exposure plan.

In both cases the correspondence 71 of the two exposure plans 57, 59 correlates with the result 73 of the evaluation of the adaptation (correlation 75). In the event that the result 73 of the evaluation of the adaptation would also then have led to a continuation of the third method 30 (decision "yes" in the fourth method step 37 in FIG. 4), the third method 30 for generation of an exposure plan (FIG. 4) is then sufficiently precise when the two exposure plans coincide within the tolerance range and, in reverse, would have led to a termination of the third method 30 (decision "no" in the fourth method step 37 in FIG. 4) when the two exposure plans do not coincide within the tolerance range.

If the verification method 50 produces no correlation 75 of the result 73 of the evaluation with the correspondence 71 of the first exposure plan and the second exposure plan, the third method 30 for generation of an exposure plan or, respectively, the computer 1 with which the third method 30 is implemented can be improved (modification 77). For example, the adaptation algorithm 17 with which the MR image 15 of the patient is registered with the reference data set 5 can be improved in that the reference method is designed more precisely. However, the evaluation algorithm 19 can also be modified (for example by adaptation of the tolerance ranges or via a modified evaluation of the adaptation) such that, using the evaluation of the adaptation beforehand, it can be more precisely determined whether a sufficiently precise exposure plan will be generated. By contrast, when the verification method 50 produces a good correlation 75 of the result 73 of the evaluation with the correspondence 75 of the first exposure plan and the second exposure plan, this indicates a sufficiently precise third method 30 (verification 79).

For example, one possibility to establish the tolerance range for the evaluation of the differences is to have multiple experienced users generate an exposure plan based on the verification data set 51 using the CT-MR combination method 55. Since the generation of an exposure plan always also depends to a certain degree on the interaction of a user, the generated exposure plans will exhibit a certain deviation among one another that, however, has no decisive influence on the success of an exposure. This range of these deviations can then define the tolerance range within which an exposure plan generated with the third method 30 according to FIG. 4 (or, respectively, with the modified third method) must lie.

Figure 5:
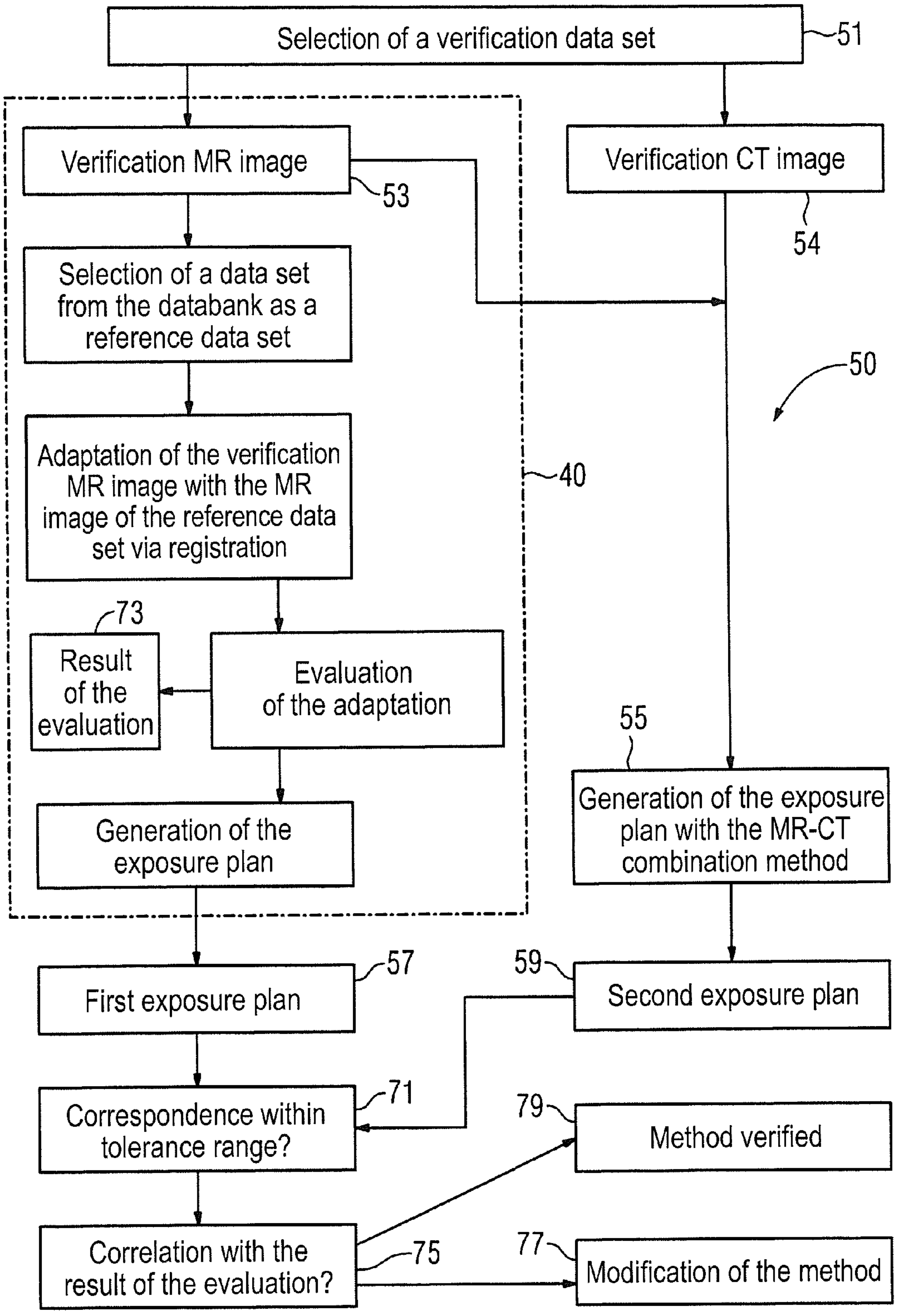
FIG. 5 is a flowchart of an embodiment of a verification procedure for quality control that can be implemented with the inventive device.
Figure 6:
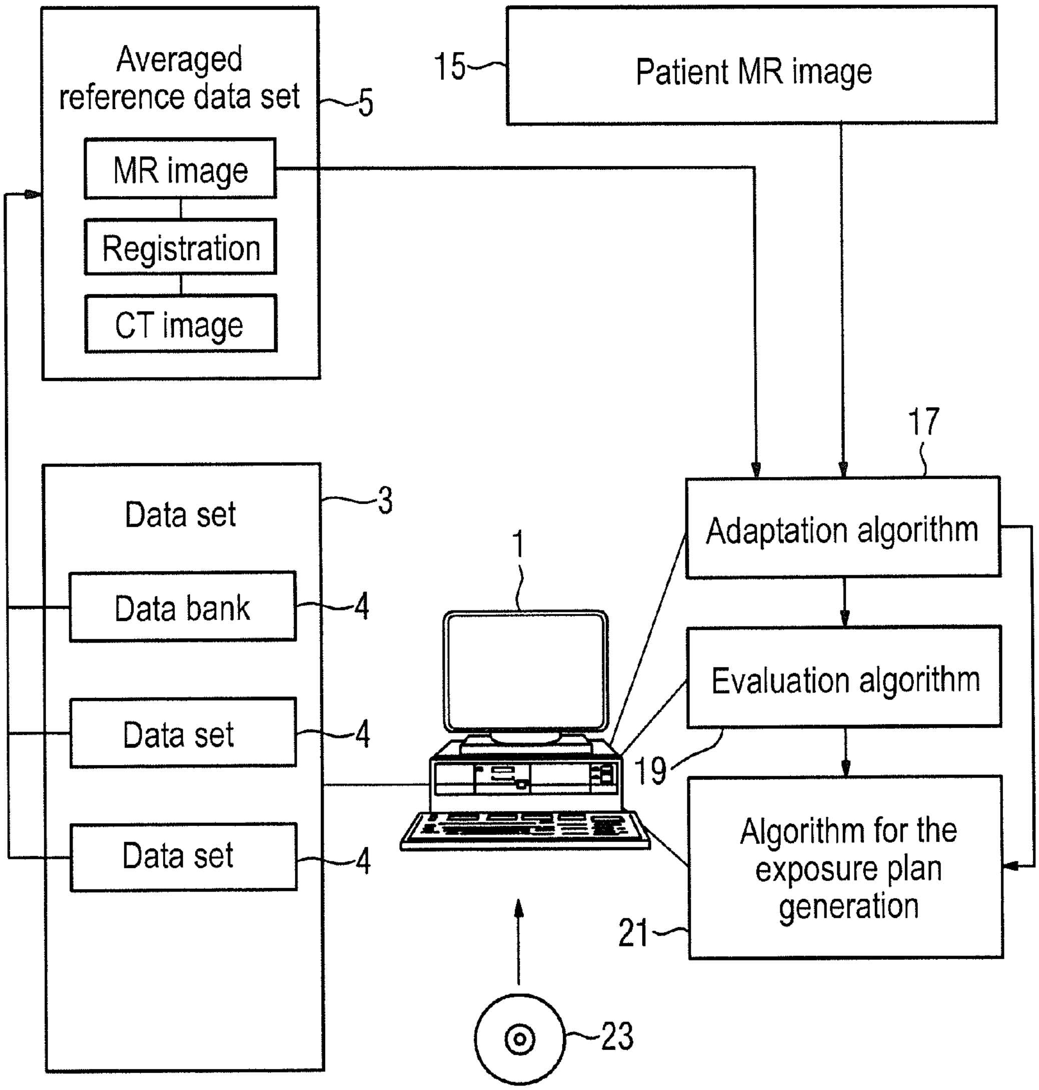
FIG. 6 schematically illustrates a further embodiment of the inventive device fashioned as a computer.

FIG. 6 shows a further embodiment of the computer 1. While a specific data set is selected from the databank 3 as a reference data set given the computer 1 shown in FIG. 1, given the computer 1 shown in FIG. 5 the reference data set 5 is determined in that the data sets 4 stored in the databank 3 are averaged. Before an averaging the data sets 4 are also registered with one another.

A reference data set 5 is hereby obtained that, although it is less detailed, is largely free of individual anatomical peculiarities. The averaging can additionally be effected once for an existing databank 3 so that the time expenditure for the averaging must only be invested once, possibly with prior registration. Furthermore, the computer 1 now requires no selection algorithm 13 (see FIG. 4), such that the method also functions if the selection algorithm 13 should fail since, for example, data for the implementation of the selection (size, weight, age etc. of the reference persons) are not entirely present.

Furthermore, a data medium 23 on which a computer program product is stored is shown in FIG. 6, constituting a computer program product (loaded into the memory of the computer 1) that equips the computer with the necessary databank interfaces and program algorithms for implementation of a method according to FIG. 4 or FIG. 5.

Although modifications and changes may be suggested by those skilled in the art, it is the intention of the inventor to embody within the patent warranted hereon all changes and modifications as reasonably and properly come within the scope of his contribution to the art.

I claim as my invention:

1. A computerized device for generating an exposure plan for irradiating a patient with therapeutic penetrating radiation that interacts with target tissue, which is surrounded by other tissue, to beneficially modify said target tissue, said therapeutic radiation being attenuated by said other tissue, said device comprising:

a computer having access to at least one reference data set for a reference body that is independent of the patient but corresponds to a region of the patient containing said target tissue and said other tissue, said reference data set comprising patient-independent information about radiation attenuation for said penetrating radiation;

said computer also having access to magnetic resonance data representing a patient magnetic resonance image of said region of the patient;

said computer comprising an adaptation unit that adapts said patient magnetic resonance image to said reference data set, to produce an adaptation between the magnetic resonance image and the reference data set;

said computer being configured to determine patient-specific attenuation for said penetrating radiation upon passage through the region of the patient, using said adaptation between the patient magnetic resonance image and the reference data set said patient-independent information about radiation attenuation for said penetrating radiation;

said computer being configured to generate an exposure plan dependent on said patient magnetic resonance image and said patient-specific attenuation for said penetrating radiation; and an output unit in communication with said computer at which said computer causes said exposure plan to be visually presented.

2. A computerized device as claimed in claim 1 wherein said computer employs data representing a computed tomography image of said reference body as said at least one reference data set.

3. A computerized device as claimed in claim 2 wherein said computer employs, as said at least one reference data set, a reference data set that also comprises data representing a magnetic resonance image of said reference body corresponding to said computed tomography image of said reference body.

4. A computerized device as claimed in claim 3 wherein said adaptation unit adapts the patient magnetic resonance image also using the magnetic resonance image in said reference data set.

5. A computerized device as claimed in claim 3 wherein said computer employs, as said at least one reference data set, a reference data set with said magnetic resonance image and said computed tomography image being in registration with each other.

6. A computerized device as claimed in claim 5 wherein said adaptation unit adapts said patient magnetic resonance image with said magnetic resonance image of said reference data set by bringing said patient magnetic resonance image into registration with said magnetic resonance image in said reference data set using a registration procedure selected from the group consisting of rigid registration procedures and elastic registration procedures.

7. A computerized device as claimed in claim 1 comprising a data bank in which said reference data set is stored together with a plurality of other reference data sets respectively for other reference bodies.

8. A computerized device as claimed in claim 7 wherein said computer comprises an administration unit that administers said data bank.

9. A computerized device as claimed in claim 8 wherein said administration device selects, as said at least one reference data set, one of said reference data sets from said data bank that exhibits a highest correspondence with said patient magnetic resonance image.

10. A computerized device as claimed in claim 7 wherein said reference data set is an average reference data set that is averaged from said further reference data sets.

11. A computerized device as claimed in claim 1 wherein said computer comprises an evaluation unit that evaluates the adaptation of the patient magnetic resonance image with said reference data set.

12. A method for generating an exposure plan for irradiating a patient with therapeutic penetrating radiation that interacts with target tissue, which is surrounded by other tissue, to beneficially modify said target tissue, said therapeutic radiation being attenuated by said other tissue, said method comprising:

(a) providing a computer with at least one reference data set representing a reference body that is independent of the patient but corresponds to a region of the patient containing said target tissue and said other tissue, said reference data set comprising patient-independent information about radiation attenuation for said penetrating radiation;

(b) providing said computer also with magnetic resonance data representing a patient magnetic resonance image of the region of the patient;

(c) in said computer, adapting said patient magnetic resonance image to said reference data set to produce an adaptation between the magnetic resonance image and the reference data set;

(d) in said computer, determining patient-specific attenuation for said penetrating radiation upon passage through the region of the patient using said adaptation between the magnetic resonance image and the reference data set and said patient-independent information about radiation attenuation for said penetrating radiation;

(e) generating an exposure plan dependent on said patient magnetic resonance image and said patient-specific attenuation for said penetrating radiation; and (f) making said exposure plan visually available from said computer.

13. A method as claimed in claim 12 wherein step (a) comprises providing said computer with data representing a computed tomography image of said reference body as said at least one reference data set.

14. A method as claimed in claim 12 wherein step (a) comprises providing said computer, as said at least one reference data set, with a reference data set that also comprises data representing a magnetic resonance image of said reference body corresponding to said computed tomography image of said reference body.

15. A method as claimed in claim 14 wherein step (b) comprises adapting the patient magnetic resonance image using the magnetic resonance image in said reference data set.

16. A method as claimed in claim 14 wherein step (a) comprises providing said computer, as said at least one reference data set, with a data set with said magnetic resonance image and said computed tomography image being in registration with each other.

17. A method as claimed in claim 16 wherein step (b) comprises adapting said patient magnetic resonance image with said magnetic resonance image of said reference data set by bringing said patient magnetic resonance image into registration with said magnetic resonance image in said reference data set using a registration procedure selected from the group consisting of rigid registration procedures and elastic registration procedures.

18. A method as claimed in claim 12 comprising storing said reference data set in a data bank together with a plurality of other reference data sets respectively for other reference bodies.

19. A method as claimed in claim 18 comprising administering said data bank in said computer.

20. A method as claimed in claim 18 comprising administering said data bank by selecting, as said at least one reference data set, one of said reference data sets from said data bank that exhibits a highest correspondence with said patient magnetic resonance image.

21. A method as claimed in claim 18 comprising generating said reference data set in said computer as an average reference data set that is averaged from said further reference data sets.

22. A method as claimed in claim 12 comprising, in said computer, evaluating the adaptation of the patient magnetic resonance image with said reference data set.

23. A method as claimed in claim 12 wherein said exposure plan is a first exposure plan and wherein step (b) comprises providing a patient computed tomography image to said computer in addition to said patient magnetic resonance image, and comprising repeating steps (a) through (c) to generate a second exposure plan using both said patient magnetic resonance image and said patient computed tomography image, and comprising verifying said first exposure plan in said computer by comparing said first exposure plan and said second exposure plan.

24. A method as claimed in claim 12 comprising storing said at least one reference data set in a data bank together with a plurality of further reference data sets for respectively different reference bodies, each of said further reference data sets comprising data representing a magnetic resonance image of the reference body for that data set and data representing a computed tomography image of the reference body for that data set, and comprising, in said computer, determining a verification data set from a plurality of said further reference data sets in said data bank, said verification data set comprising a verification magnetic resonance image and a verification computed tomography image, and comprising generating said exposure plan, as a first exposure plan, using said verification magnetic resonance image as said patient magnetic resonance image, and comprising repeating steps (a) through (c) to generate a second exposure plan using both the verification magnetic resonance image and the verification computed tomography image as the patient magnetic resonance image, and comprising verifying said first exposure plan in said computer by comparing said first exposure plan and said second exposure plan.

25. A non-transitory computer-readable storage medium encoded with a data structure for generating an exposure plan for irradiating a patient with therapeutic penetrating radiation that interacts with target tissue, which is surrounded by other tissue, to beneficially modify said target tissue, said therapeutic radiation being attenuated by said other tissue, said storage medium being loadable into a computer, said computer:

(a) having access to at least one reference data set representing a reference body that is independent of the patient but corresponds to a region of the patient containing said target tissue and said other tissue, said reference data set comprising patient-independent information about radiation attenuation for said penetrating radiation, and also (b) having access to magnetic resonance data representing a patient magnetic resonance image of the region of the patient, said data structure causing said computer to:

(c) adapt said patient magnetic resonance image to said reference data set, to produce an adaptation between the magnetic resonance image and the reference data set;

(d) determine patient-specific attenuation for said penetrating radiation upon passage through the patient using said adaptation between the patient magnetic resonance image and the reference data set and said patient-independent information about radiation attenuation for said penetrating radiation;

(e) generate an exposure plan dependent on said patient magnetic resonance image and said patient-specific attenuation for said penetrating radiation; and (f) cause said exposure plan to be visually presented from said computer.

26. A computer-readable medium encoded with a data structure as claimed in claim 25 wherein said exposure plan is a first exposure plan and wherein said computer has access to a patient computed tomography image to said computer in addition to said patient magnetic resonance image, and wherein said data structure causes said computer to repeat steps (a) through (c) to generate a second exposure plan using both said patient magnetic resonance image and said patient computed tomography image, and to verify said first exposure plan by comparing said first exposure plan and said second exposure plan.

27. A computer-readable medium encoded with a data structure as claimed in claim 25 wherein said computer has access to a plurality of further reference data sets for respectively different reference bodies, each of said further reference data sets comprising data representing a magnetic resonance image of the reference body for that data set and data representing a computed tomography image of the reference body for that data set, and wherein said data structure causes said computer to determine a verification data set from a plurality of said further reference data sets, said verification data set, comprising a verification magnetic resonance image and a verification computed tomography image, and to generate said exposure plan, as a first exposure plan, using said verification magnetic resonance image as said patient magnetic resonance image, and to repeat steps (a) through (c) to generate a second exposure plan using both the verification magnetic resonance image and the verification computed tomography image as the patient magnetic resonance image, and to verify said first exposure plan by comparing said first exposure plan and said second exposure plan.

* * * * *